US00PP22642P2

(12) United States Plant Patent
Crook

(10) Patent No.: US PP22,642 P2
(45) Date of Patent: Apr. 10, 2012

(54) ***BEGONIA* PLANT NAMED 'BRXPE11'**

(50) Latin Name: *Begonia rex cultorum*
Varietal Denomination: BRXPE11

(76) Inventor: Gary Crook, Scotts Mills, OR (US)

( * ) Notice: Subject to any disclaimer, the term of this patent is extended or adjusted under 35 U.S.C. 154(b) by 0 days.

(21) Appl. No.: 12/925,777

(22) Filed: Oct. 29, 2010

(51) Int. Cl.
*A01H 5/00* (2006.01)

(52) U.S. Cl. ..... Plt./343

(58) Field of Classification Search ..... Plt./343
See application file for complete search history.

*Primary Examiner* — Annette Para

(57) ABSTRACT

A new and distinct *Begonia rex cultorum* cultivar named 'BRXPE11' is disclosed, characterized by bright foliage with a metallic sheet, and vigorous year round growth, including during the dark winter months. The new variety is a *Begonia*, and is normally used as an ornamental plant.

1 Drawing Sheet

Figure 1:
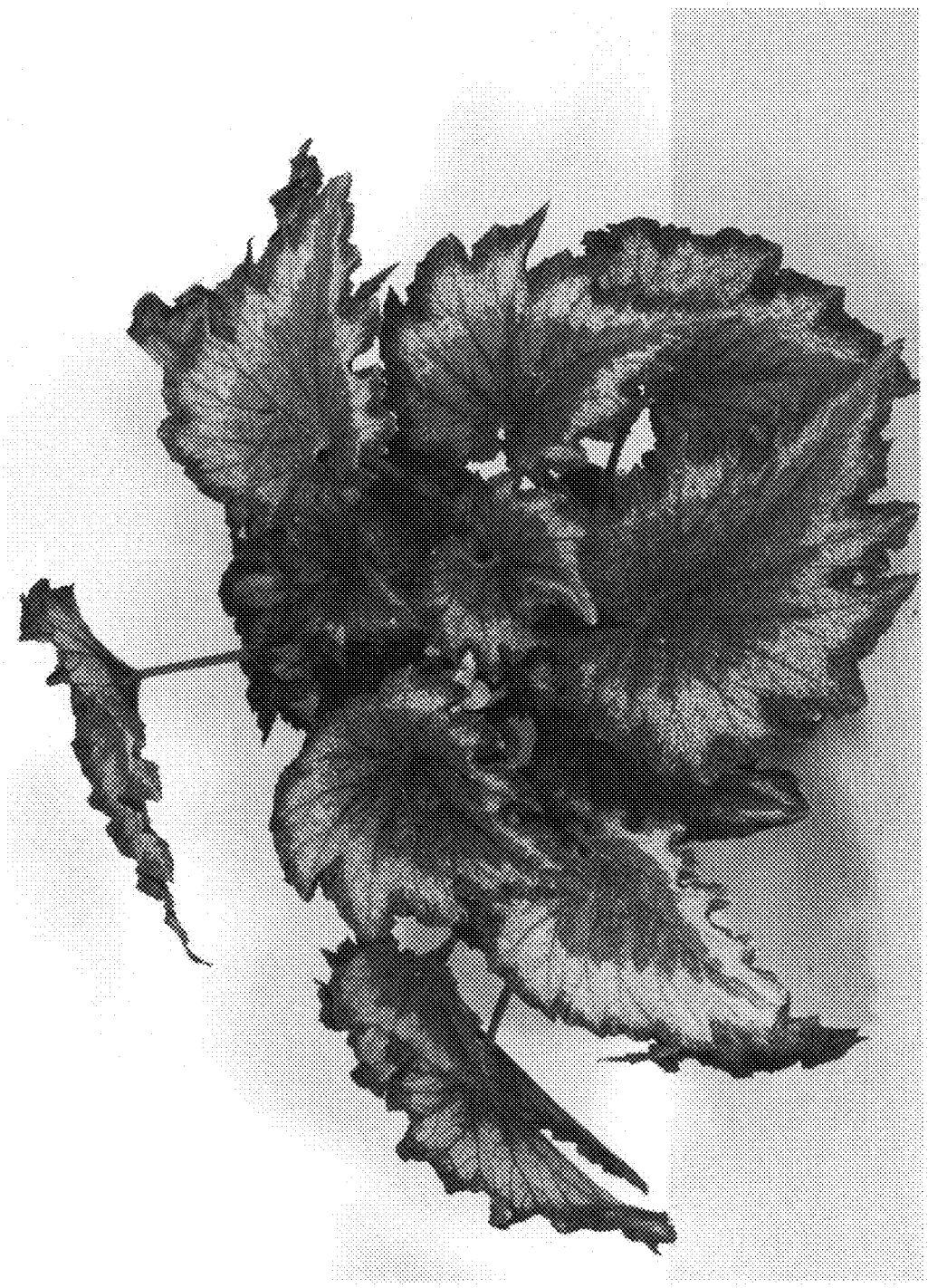

Latin name of the genus and species: *Begonia rex cultorum.* Variety denomination: 'BRXPE11'.

BACKGROUND OF THE INVENTION

The new cultivar is a product of a planned breeding program. The new variety originated as the result of a crossing performed in 2008 of the unpatented seed parent variety *Begonia rex cultorum* 'Lalome' with the pollen parent, the unpatented variety *Begonia rex cultorum* 'Red Rocket.' The new variety was discovered by the inventor, Gary Crook, a citizen of the United States, at a commercial greenhouse in Scotts Mills, Oreg. during 2008, among a planting of seedlings resulting from the previously mentioned crossing.

Asexual reproduction of the new cultivar 'BRXPE11' was first performed in Scotts Mills, Oreg. in 2009, by vegetative leaf cuttings. 'BRXPE11' has since produced several generations by vegetative leaf cuttings and has shown that the unique features of this cultivar are stable and reproduced true to type.

SUMMARY OF THE INVENTION

The cultivar 'BRXPE11' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BRXPE11.' These characteristics in combination distinguish 'BRXPE11' as a new and distinct *Begonia rex cultorum* cultivar:

1. Bright, metallic looking foliage colored silver and magenta.
2. Vigorous, year round growth.
3. Unique rapid growth habit at lower temperatures.
4. Flexible petioles, resisting breakage.
5. Medium sized leaf, for this category of *Rex Begonia.*

PARENT COMPARISON

Plants of the new cultivar 'BRXPE11' are similar to plants of the seed parent variety, *Begonia rex cultorum* 'Lalome' in most horticultural characteristics. However, plants of the new cultivar 'BRXPE11' produce foliage that is magenta and silver green colored, whereas 'Lalome' produces a lavender colored foliage. Additionally, the new variety produces leaves that are 20-25% smaller than 'Lalome' and shorter petioles as well.

Plants of the new cultivar 'BRXPE11' are similar to plants of the pollen parent variety, *Begonia rex cultorum* 'Red Rocket' in most horticultural characteristics. However, plants of the new cultivar 'BRXPE11' produce foliage that is silver green and magenta colored, whereas 'Red Rocket' produces red and black colored foliage. Additionally, the new variety produces leaves that are 20-25% smaller than 'Red Rocket.' Additional differences are that 'Red Rocket' has brittle petioles that are prone to breakage, while 'BRXPE11' produces flexible petioles, and 'BRWCA17' continues to grow during the short days of winter, while 'Red Rocket' stops growing during short days.

COMMERCIAL COMPARISON

Plants of the new cultivar 'BRXPE11' are similar to plants of the unpatented commercial variety, *Begonia rex* hybrid 'Merry Christmas' in most horticultural characteristics. However, plants of the new cultivar 'BRXPE11' grow faster, both under winter and summer conditions. Specifically, 'BRXPE11' can be commercially finished 2 weeks faster under summer conditions, and 4 weeks faster under winter conditions than 'Merry Christmas.' Additionally the new variety grows significantly faster under lower night temperatures, and produces a fuller, bushier plant under winter conditions than 'Marvelous.'

Plants of the new cultivar 'BRXPE11' are similar to plants of the unpatented commercial variety, *Begonia rex cultorum* 'Marvelous' in most horticultural characteristics. However, plants of the new cultivar 'BRXPE11' grow faster, both under winter and summer conditions. Specifically, 'BRXPE11' can be commercially finished 2 weeks faster under summer conditions, and 4 weeks faster under winter conditions than 'Marvelous.' Additionally the new variety grows significantly faster under lower night temperatures, and produces a fuller, bushier plant under winter conditions than 'Marvelous.'

BRIEF DESCRIPTION OF THE PHOTOGRAPH

The accompanying photograph in FIG. 1 illustrates in full color a typical plant of 'BRXPE11' grown in a greenhouse.

The pot size is a commercial 6 inch pot. The plant shown is approximately 6 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'BRXPE11' plants grown in a commercial controlled greenhouse in Oxnard, Calif. Temperatures ranged from 15° C. to 28° C. during the day and 18° C. to 22° C. at night No artificial light, photoperiodic treatments or chemical treatments were given to the plants. Measurements and numerical values represent averages of typical plant types.

Botanical classification: *Begonia rex cultorum* 'BRXPE11'

Age of plant described: Approximately 6 months.

Container size of plant described: 6 inch pot.

PROPAGATION

Type of propagation typically used: Vegetative leaf cuttings.

Time to roots: About 25 days at approximately 20° C.

Root description: Dense and fibrous.

PLANT

Growth habit: Upright growing, fleshy annual.

Pot size of plant described: 6 inch.

Height: Approximately 29 cm.

Plant spread: Approximately 47 cm.

Growth rate: Rapid.

Branching characteristics: Basally emerging foliage, no actual branches, only petioles.

FOLIAGE

*Type.*—Single, basally emerging foliage and long petioles.

*Orientation.*—Outwardly or upwardly facing foliage. Approximately 75° to 90° angle from petiole.

*Strength.*—Very strong, and flexible, resists breakage.

*Texture, top surface.*—Rugulose, with infrequently occurring, very fine, appressed hairs, approximately 0.3 to 0.4 cm in length and colored near RHS White N155A.

*Texture lower surface.*—Rugulose. Main surface non-pubescent, veins mildly pilose. Hairs approximately 0.1 cm long, colored near RHS White N155C.

*Appearance.*—Metallic and leathery appearance to upper surface. Lower surface leathery, matte.

*Quantity.*—Approximately 12 fully expanded mature leaves and approximately 12 immature leaves.

*Shape of blade.*—Reniform.

*Apex.*—Acute.

*Base.*—Cordate, asymmetrical.

*Margin.*—Dentate. Shallow, acute lobes.

*Aspect.*—Recurved.

Mature leaves:

*Average length.*—Approximately 18 to 20 cm.

*Average width.*—Approximately 12 cm.

*Color.*—Mature foliage upper side: Beginning near petiole attachment, width of approximately 1 cm: RHS Greyed-Green N189A, speckles of Greyed-Purple 187A. Next section, approximately 2 cm, Greyed-Purple 187B with irregular lines near Greyed-Purple N187A. Next section, approximately 2 cm, Greyed-Green 193A with irregular lines near Green 137A. Margin, approximately 1 to 1.5 cm from edge, Greyed-Purple 187B with irregular lines of Greyed-Purple N186B. Mature foliage under side: Near petiole attachment: RHS Greyed-Purple 187A. Mid section Green 138B, flushed Greyed-Purple 187A near veins. Margin, approximately 1 cm from leaf edge, Greyed-Purple 187A.

*Venation.*—Type: Palmate. Venation color upper side: From Petiole attachment to approximately ⅔ length of blade colored near RHS Greyed-Purple N186A. Outer ⅓ near Greyed-Green 191A. Venation color under side: Near RHS Greyed-Green 189A.

Immature leaves:

*Average length.*—Approximately 12 cm.

*Average width.*—Approximately 8 cm.

*Color.*—Immature foliage upper side: Near petiole attachment: RHS Greyed-Green N189A, speckles of Greyed-Purple 186C. Mid section Greyed-Green 191C with thick, irregular lines near Green 138B. Margin, approximately 0.5 cm from edge, Greyed-Purple N186B, speckles Greyed-Purple 186A. Immature foliage under side: Near petiole attachment: RHS Greyed-Purple 187A. Mid section Green 138B, flushed Greyed-Purple 187A near veins. Margin, approximately 0.5 cm from leaf edge, Greyed-Purple 187A.

*Venation.*—Type: Palmate. Venation color upper side: From Petiole attachment to approximately ⅔ length of blade colored near RHS Greyed-Purple N187A. Outer ⅓ near Greyed-Green 191A. Venation color under side: Near RHS Greyed-Purple 187A.

*Petiole.*—Length: Average Range Approximately 13 cm. Diameter: Approximately 0.6 cm. Color: Near RHS Greyed-Red 181C. Texture: Pilose. Hairs approximately 0.3 cm long, colored near RHS White 155C.

*Stipule description.*—Length: Approximately 1.2 cm. Length includes 0.2 cm awn. Diameter: Approximately 0.7 cm. Apex: Aristate. Base: Truncate. Color: Near RHS Greyed-Purple 185B, upper and lower. Texture: Upper Surface: Glabrous. Lower Surface: Very sparsely pilose.

FLOWER

Flowering habit: Rarely flowering

Inflorescence and flower type and habit: Single flowers arranged in axillary cymes. Cymes held deep under the foliage, approximately 1 or 2 open flowers per cyme. Normally one flower or cyme per plant open at one time.

Cyme size(when 2 flowers present):

*Diameter.*—Approximately 5.5 cm.

*Height.*—Approximately 5.0 cm.

Flower longevity on plant: About 2 days.

Persistent or self-cleaning: Self-Cleaning.

Bud:

*Shape.*—Flattened sphere.

*Length.*—Approximately 1 cm.

*Diameter.*—Approximately 1 cm.
*Color.*—Near RHS Greyed-Red 179D. Apex and base near Yellow-Green 144B.
*Texture.*—Pilose.

Flower size:
*Diameter.*—Approximately 3.4 cm.
*Depth.*—Approximately 1.8 cm.

Tepals:
*Quantity.*—Approximately 5.
*Arrangement.*—Radial.
*Length.*—Approximately 1.8 cm.
*Width.*—Approximately 1.2 cm.
*Shape.*—Oval.
*Apex.*—Obtuse.
*Base.*—Rounded.
*Margin.*—Entire.
*Aspect.*—Flat.
*Texture, upper surfaces.*—Glabrous.
*Texture, lower surfaces.*—Glabrous.
*Upper surface appearance.*—Shiny.
*Lower surface appearance.*—Matte.
*Color.*—When opening, upper surface: Near RHS White N155C with flush of Red 54C. When opening, lower surface: Near RHS Red 54C. Fully opened, upper surface: Near RHS White N155D. Fully opened, lower surface: Near RHS White N155D. Fading to, both sides: Near RHS White N155D.

Flower bracts: Not observed.

Peduncles:
*Length.*—Average Approximately 10 cm.
*Diameter.*—Approximately 0.2 cm.
*Strength.*—Moderate, flexible.
*Texture.*—Glabrous.
*Appearance.*—Matte.
*Color.*—Near RHS Yellow-Green 146A.

Pedicels:
*Length.*—Average Approximately 1.5 cm.
*Diameter.*—Approximately 0.1 cm.
*Angle.*—About 15° to the peduncle.
*Strength.*—Moderate, flexible.
*Texture.*—Glabrous.
*Appearance.*—Shiny.
*Color.*—Near RHS Red 54 C near lower end, near Yellow-Green 146C near flower attachment.

Fragrance: Sweet.

REPRODUCTIVE ORGANS

Stamens:
*Number.*—Approximately 3.

Anthers: Description: Heavily ruffled. Length: Approximately 0.4 cm. Color: Near RHS Yellow 12A. Pollen: Not observed.

Pistil:
*Number.*—1.
*Length.*—Approximately 0.5 cm.
*Style.*—Length: Approximately 0.2 cm. Color: Near RHS Green-Yellow 1C.
*Stigma.*—Shape: Columnar. Color: Near RHS Green-Yellow 1C. Ovary Color: RHS Green-Yellow 1C.

OTHER CHARACTERISTICS

Seeds and fruits: Not Observed.

Disease/pest resistance: Neither resistance nor susceptibility to diseases or pests has been observed in this variety.

Temperature tolerance: The new variety tolerates temperatures from approximately 0° to 35° C.

What is claimed is:

1. A new and distinct cultivar of *Begonia* plant named 'BRXPE11' as herein illustrated and described.

* * * * *